United States Patent [19]
Mikulicz

[11] 4,239,931
[45] Dec. 16, 1980

[54] HF ALKYLATIOR PROCESS
[75] Inventor: Michael Z. Mikulicz, Palatine, Ill.
[73] Assignee: UOP Inc., Des Plaines, Ill.
[21] Appl. No.: 91,659
[22] Filed: Nov. 5, 1979
[51] Int. Cl.³ .............................................. C07C 2/58
[52] U.S. Cl. .................... 585/723; 585/710; 585/719
[58] Field of Search ...................... 585/710, 719, 723

[56] References Cited
U.S. PATENT DOCUMENTS

| | | | |
|---|---|---|---|
| 3,249,650 | 5/1966 | Femske | 585/710 |
| 3,560,587 | 2/1971 | Borst | 585/714 |
| 3,686,354 | 8/1972 | Hervert | 585/331 |
| 3,713,615 | 1/1973 | Jones | 202/154 |
| 3,804,918 | 4/1974 | Henderson | 585/723 |
| 3,928,486 | 12/1975 | Sobel | 585/723 |
| 3,981,942 | 9/1976 | Zabransky | 585/723 |
| 4,046,516 | 9/1977 | Burton et al. | 585/723 |

Primary Examiner—Curtis R. Davis
Attorney, Agent, or Firm—James R. Hoatson, Jr.; Robert W. Welch; William H. Page, II

[57] ABSTRACT

A process for the hydrofluoric acid-catalyzed alkylation of an isoparaffin with an olefin in a gravity-flow hydrofluoric acid alkylation reaction system. The process is effected without benefit of an acid regenerator. Regeneration is effected an isostripper column, and catalyst-contaminating polymeric products of the alkylation are recovered in the normally liquid alkylate product substantially free of hydrofluoric acid.

11 Claims, 1 Drawing Figure

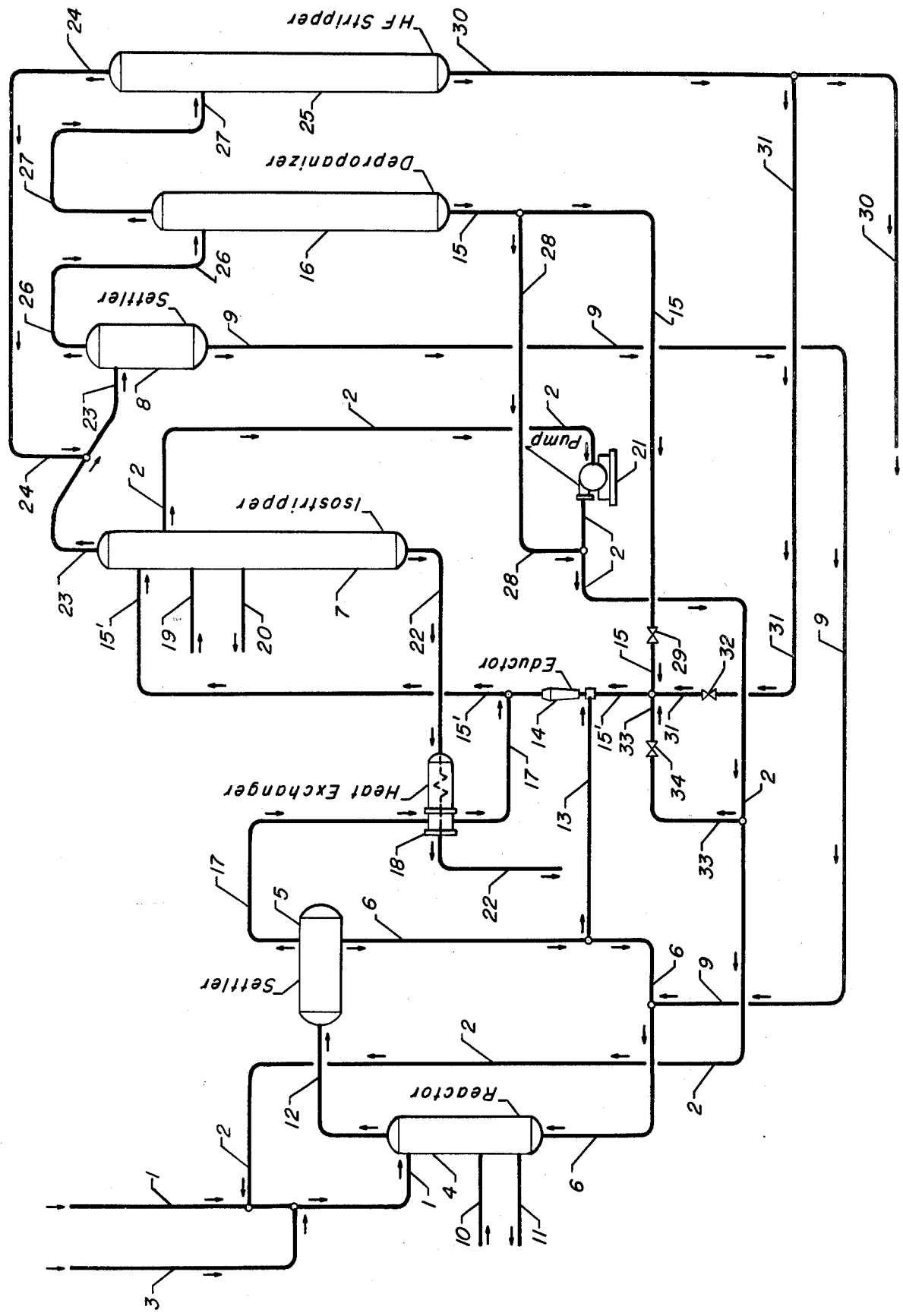

HF ALKYLATION PROCESS

This invention relates to a process for the acid-catalyzed alkylation of an isoparaffin with an olefin, or an olefin-acting compound, as the alkylating agent. The acid-catalyzed alkylation of a normally gaseous isoparaffinic hydrocarbon with a normally gaseous olefinic hydrocarbon to yield a normally liquid, higher molecular weight, isoparaffinic hydrocarbon product, has long been recognized by the petroleum industry as a valuable tool in the manufacture of gasoline products high in octane value.

The acid-catalyzed alkylation process herein contemplated is almost invariably a hydrofluoric acid-catalyzed process which, since its inception, has experienced many changes and improvements with respect to unit design and operating techniques. The present invention embodies a modified acid catalyst regeneration scheme affording a significant improvement in operational stability as well as certain economic advantages.

The prior art is replete with publications, inclusive of issued patents, directed toward the acid-catalyzed alkylation of an isoparaffin with an olefin alkylating agent. This is particularly true with respect to hydrofluoric acid-catalyzed alkylation which traces its development over an approximate 30 year period. It is believed that a brief description of the more recent innovations will serve to illustrate the utility of the present invention and define the area to which it applies.

U.S. Pat. No. 3,560,587 describes the hydrofluoric acid-catalyzed alkylation of an isoparaffin with an olefin in a system incorporating a reaction cooler, reaction soaker and an acid settler. The greater portion of the hydrofluoric acid which settles out in the acid settler is recycled to the cooled reaction zone for further contact with the reaction mixture therein. The remaining portion is indicated as being transferred to suitable acid regeneration facilities for the separation of polymer products.

U.S. Pat. No. 3,686,354 is fairly illustrative of a complete hydrofluoric acid-catalyzed alkylation system including reaction vessels, reactor effluent separation means for the recovery of acid catalyst, and for the recovery of alkylate product. In this system, the alkylate product is separated into a relatively high octane fraction and a relatively low octane fraction, the latter being further treated with additional isoparaffin and acid catalyst. An integral part of the process as illustrated involves the introduction of at least a portion of the recovered acid catalyst into a suitable regeneration system for the removal of polymer products formed during the alkylation reaction.

U.S. Pat. No. 3,713,615 is specifically directed toward a fractionation vessel for utilization in the separation of the alkylation reactor effluent. It is contemplated therein that at least a portion of the recovered acid catalyst will be subjected to regeneration in order to separate polymer products.

U.S. Pat. No. 3,249,650 offers another fairly complete illustration of a hydrofluoric acid-catalyzed alkylation process in which a portion of the separated catalyst is regenerated to recover polymer products. In this instance, the polymer products are utilized to supply a portion of the required heat energy to the process.

Although the innovative features vary, the foregoing patents disclose a common practice—the regeneration of at least a portion of the separated hydrofluoric acid catalyst for the purpose of removing polymer products formed during the alkylation reaction. Historically, the polymer products have been removed from the alkylation process only periodically as required to obviate any adverse affect on the stability of the alkylation reaction, and the activity and efficiency of the alkylation catalyst. Furthermore, it had heretofore been considered that the removal of said polymer products as a portion of the alkylate product was undesirable in that such practice effected a degradation of said product. The prior art technique of periodic removal of polymer products has several disadvantages. For example, in a hydrofluoric acid-catalyzed alkylation process, polymer products are formed at a rate approximating 10 to 20 bbls/day for a unit designed for a charge capacity of about 10,000 bbls/day. Therefore, utilizing the prior art technique, the acid catalyst regenerator is placed in on-stream service about one day out of every seven to ten days. Units which are "pushed" beyond design capacity will generally regenerate the acid catalyst more frequently—about two to six days—or continuously, depending on the degree to which the capacity of the unit has been exceeded. This type of sporadic operation inherently results in temporary but significant upsets regarding operational stability. In addition, this prior art technique requires the installation of relatively expensive equipment which is frequently idled.

In a copending U.S. application Ser. No. 670,491, there is disclosed a hydrofluoric acid-catalyzed alkylation process which functions in the absence of an acid regenerator thus precluding any upset in operational stability resulting from the periodic placement of said regenerator on stream. Polymer products are recovered in the normally liquid product without adverse effect on product quality, and said product is recovered substantially free of the hydrofluoric acid catalyst. In addition, an acid catalyst-unreacted isoparaffin mixture is recovered for ultimate recycle to the alkylation reactor substantially free of polymer products and other foreign matter, such as acid sulfur oils and the like. In lieu of an acid regenerator, that portion of the hydrofluoric acid catalyst recovered from the acid settler for treatment in the acid regenerator is instead charged to the isostripper column for treatment therein, said acid catalyst being first recombined with the hydrocarbon phase recovered from the acid settler, and charged to the isostripper column in admixture therewith. In the isostripper column, the principal difficulty encountered is in the separation of hydrofluoric acid from the polymer products recovered in the alkylate product. While the polymer products have been shown to have little if any detrimental effect respecting product quality, either as to octane rating or color, the presence of any substantial amount of hydrofluoric acid effects a definite degradation thereof.

It was observed that, when the amount of acid recovered from the acid settler for regeneration exceeds the solubility thereof in the hydrocarbon phase recovered from said acid settler and charged to the isostripper in admixture therewith, said acid will often appear in the normally liquid alkylate product recovered as a bottoms stream from the isostripper column. The aforesaid difficulty was therefore overcome by the device of raising the temperature of the hydrocarbon phase recovered from the acid settler to effect an improved solubility of the acid catalyst therein. Hydrofluoric acid recovered from the acid settler for regeneration is admixed with the heated hydrocarbon phase and charged to the isostripper column. The isoparaffinic stream being recovered overhead from the isostripper column effectively strips the hydrofluoric acid from the acid-hydrocarbon stream and the polymer products contained therein, and said acid is recovered overhead in admixture with said isoparaffin stream substantially free of polymer products, said polymer products being recovered in the normally liquid alkylate product substantially free of hydrofluoric acid.

The present invention embodies an improvement to the last mentioned alkylation process, an improvement designed to provide a motive force for the movement of hydrofluoric acid catalyst to the isostripper column for regeneration in a gravity-flow hydrofluoric acid alkylation reactor system.

In one of its broad aspects, the present invention embodies a process for the hydrofluoric acid-catalyzed alkylation of an isoparaffin with an olefin utilizing an isoparaffin stripping column-integrated acid catalyst regeneration system which comprises the steps of reacting said olefin with said isoparaffin in an alkylation reaction zone in admixture with a hydrofluoric acid catalyst at alkylation reaction conditions resulting in a reaction product effluent comprising a normally liquid alkylate product, unreacted isoparaffin, hydrofluoric acid catalyst, and polymer products; introducing said reaction zone effluent into a separation zone, and settling said mixture into an acid-immiscible hydrocarbon phase and a polymer-containing acid phase; recovering and recycling a first portion of said acid phase to said reaction zone; recovering and heating said hydrocarbon phase to increase the solubility potential of hydrofluoric acid therein; recovering and transferring a second portion of said acid phase to the suction inlet of an eductor and entraining said acid phase in a $C_3$-$C_4$ paraffinic hydrocarbon pumping fluid charged therethrough; admixing the acid-containing eductor effluent with said heated hydrocarbon phase; and, introducing the resulting mixture into a stripping column and stripping a polymer-free acid catalyst therefrom by means of a counterflowing isoparaffin-containing stream, separating an intermediate isoparaffin fraction from said column, and recovering a polymer-containing, normally liquid, alkylate bottoms product.

As hereinbove set forth, this invention is directed toward an improvement in a process for the alkylation of an isoparaffin with an olefin, or an olefin-acting compound. Although particularly adapted to the alkylation of isobutane with a butylene-containing olefinic stream, the process is also adaptable for utilization with other isoparaffinic and olefinic feedstocks for the purpose of producing motor fuel or aviation alkylates. Suitable isoparaffinic hydrocarbons are those having from about 4 to about 7 carbon atoms per molecule, including isobutane, isopentane, neopentane, one or more of the isohexanes and various branched-chain heptanes. Similarly, the olefinic reactant contains from about 3 to about 7 carbon atoms per molecule, and includes propylene, 1-butene, 2-butene, isobutylene, the isomeric amylenes, hexenes, and various heptenes.

The alkylation reaction mixture comprises a hydrofluoric acid catalyst, an isoparaffin and an olefinic hydrocarbon. Hydrofluoric acid is utilized in an amount generally sufficient to provide an acid catalyst/hydrocarbon volume ratio within the reaction zone of from about 0.5 to about 3. Hydrofluoric acid, as employed throughout the present specification and appended claims, is intended to include catalysts where hydrogen fluoride is the essential active ingredient. It is, therefore, within the scope of the present invention to employ substantially anhydrous hydrogen fluoride, hydrofluoric acid, or hydrogen fluoride containing various additives or promoters. As a general practice, commercial anhydrous hydrogen fluoride will be charged to the alkylation system as fresh catalyst. It is possible to use hydrogen fluoride containing as much as about 10% water; however, excessive dilution with water is undesirable since it tends to reduce the alkylating activity of the catalyst and introduces severe corrosion problems into the system. In order to reduce the tendency of the olefinic portion of the hydrocarbon feedstock to undergo polymerization prior to alkylation, the molar proportion of isoparaffin to olefinic hydrocarbon within the alkylation reaction zone is maintained at a value greater than about 1:1, up to about 20:1, and preferably from about 3:1 up to about 15:1. A common practice entails utilizing a plurality of feed loci.

Alkylation reaction conditions include temperatures in the range of about 0° to about 200° F., and preferably from about 30° to about 110° F. In view of the fact that the alkylation reaction is highly exothermic, suitable means for removing heat from the reaction zone is generally provided. In general practice, the reaction zone is designed such that it functions as a form of heat-exchanger. Alkylation pressures are sufficiently high to maintain the hydrocarbons and hydrofluoric acid catalyst in substantially liquid phase; that is, from about 15 psig. to about 600 psig. The contact time in the alkylation reactor is most conveniently expressed in terms of a space-time relationship which is defined as the volume of catalyst within the reactor, or contacting zone, divided by the volume rate per minute of hydrocarbon reactants charged to the zone. Usually, the space-time relationship will be less than about 5 minutes and preferably less than about 2 minutes.

As is the common current practice, the product effluent from the alkylation reaction zone is discharged into a first acid settler sized and designed to provide an average residence time therein of from about 0.01 to about 0.5 hour, depending on the composition and character of the alkylation reaction mixture charged thereto, and sufficient to provide an acid-immiscible hydrocarbon phase and a settled acid phase substantially free of hydrocarbons. The settled hydrofluoric acid is recycled to the reaction zone in admixture with regenerated hydrofluoric acid as hereinafter set forth. The reaction zone effluent generally contains a relatively minor proportion of polymer products and other foreign matter formed during the alkylation reaction. These polymer products appear in the hydrofluoric acid phase removed from the lower portion of the settler. In order to prevent the buildup of polymer products within the reaction system, a relatively minor proportion of the polymer product-containing settled acid phase is typically introduced into an acid regenerator. In a typical prior art unit, processing approximately 10,000 bbls/day of hydrocarbon reactant, the regenerator vessel is approximately 20 feet in length, and consists of approximately 14 feet of bubble cap trays and about 6 feet in the lower portion serving as a collection zone for the polymer products. In general, prior art processes utilize the acid regenerator on a periodic basis in view of the fact that improved operating techniques have resulted in a further decrease in the overall quantity of polymer products produced. On the basis of approximately 100 bbls/day of hydrofluoric acid containing polymer products, the acid-regenerator will be employed in cycles approximately 7 to about 10 days, therefore processing about 700 to about 1000 barrels hydrofluoric acid. The quantity of polymer products so recovered will range from about 5% to about 20% by volume of the total charge to the acid-regenerator. Recovered hydrofluoric acid is recycled to the alkylation reaction zone in admixture with the settled acid. Such a periodic use of the acid regenerator inherently leads to operational difficulties attendant upsets in the stable operation occurring each time the acid regenerator is placed on stream, and subsequently taken out of the system. In those units in which the periodic use of the acid regenerator is not employed, but rather is on stream continuously, an excessive amount of hydrofluoric acid, with respect to the quantity of polymer products, are necessarily introduced thereto. In accordance with the present process, the acid regenerator is removed from the system.

As hereinafter described in greater detail with reference to the accompanying drawing, the present process functions in the absence of an acid regenerator, and that portion of the settled acid normally treated in the acid regenerator is instead introduced into the isostripper column in admixture with the hydrocarbon phase recovered from said settler. Pursuant to the present invention, said acid is transferred to said isostripper column by means of an eductor, the acid being transferred to the suction inlet of said eductor and entrained in a $C_3$–$C_4$ paraffinic hydrocarbon pumping fluid charged to said eductor at a relatively high pressure. The eductor herein contemplated is a device in widespread use and amply described in the literature. For example, eductors, or ejectors, are described at pages 6–29 to 6–32 of the Fourth Edition of Perry's Chemical Engineer's Handbook (1963), McGraw-Hill Book Co., a $C_3$–$C_4$ paraffinic hydrocarbon stream being in the present case utilized as the primary motive or high pressure stream charged to the eductor. The $C_3$–$C_5$ paraffinic hydrocarbon steam is preferably a recycled depropanizer column bottoms stream recovered from said column at a pressure of from about 190 to about 340 psi. A recycled hydrofluoric acid stripper column bottoms stream recovered from said column at a pressure of from about 195 to about 345 psi is another suitable $C_3$–$C_5$ paraffinic hydrocarbon stream, as is the isobutane stream recovered from the isostripper column at a pressure of from about 125 to about 175 psi.

The acid and hydrocarbon streams are separately recovered from the acid settler at a pressure of from about 175 to about 225 psi, and at a temperature generally in the range of from about 80° to about 105° F. As practiced herein, only the temperature of the hydrocarbon stream is increased to a temperature of from about 125° to about 200° F. to increase the solubility potential of the hydrofluoric acid therein. In accordance with the process of this invention, the acid-containing eductor effluent is admixed with the heated hydrocarbon stream, and the resulting mixture is introduced into the isostripper column.

A normally liquid alkylate product is recovered from the isostripper column as a bottoms stream containing the polymer products. Propane, a portion of the unreacted isobutane, and hydrofluoric acid are recovered from the isostripper column as an overhead stream and introduced into a second acid settler from which hydrofluoric acid is recovered and recycled to the alkylation reactor substantially free of polymer products. The bulk of the unreacted isobutane is taken from the isostripper column as a sidecut and recycled to the alkylation reactor or, if so desired, recycled to the aforesaid eductor as the motive force thereto.

The hydrocarbon phase from the second acid settler is taken overhead and introduced into a depropanizer column from which isobutane is removed as a bottoms fraction and preferably recycled to said eductor as the motive force thereto, or recycled in part to said eductor and in part to the alkylation reactor. A principally vaporous phase, predominantly propane containing a minor amount of hydrofluoric acid, is withdrawn overhead from the depropanizer column and introduced into a hydrofluoric acid stripping column from which hydrofluoric acid is removed overhead and recycled to said second acid settler for ultimate recycle to the alkylation reactor. Propane is typically recovered from the bottom of the acid stripping column and sent to storage or, if so desired, recycled to said eductor as the motive force thereto.

The further description of the process of this invention is presented with reference to the attached drawing representing one preferred embodiment of the invention. In the drawing, the process is presented by means of a simplified flow diagram from which such details as pumps, instrumentation and controls, quench systems, heat exchange and heat recovery circuits, valving, startup lines, and similar hardware, have been omitted as not essential to an understanding of the process. The use of such miscellaneous hardware to modify the process illustrated will be evident to those skilled in the petroleum refining arts.

The drawing is described in conjunction with a commercially scaled unit designed for the alkylation of isobutane with a mixed olefin feed containing propylene, butylenes and amylenes in an exchanger type alkylation reactor. The olefinic hydrocarbon stream, at about 5,938 bbls/day, enters the process via line 1, make-up isobutane is introduced via line 3, and field butane, at about 1,000 bbls/day, is introduced into the process by way of line 19, the isobutane-rich portion thereof being recycled by way of line 2 to combine with the olefinic hydrocarbon and make-up isobutane streams in line 1. From these fresh feed streams, a full boiling range, normally liquid alkylate product having a Reid vapor pressure of about 7 pounds is produced.

With reference to the drawing, an olefinic feedstock, such as is produced in a fluid catalytic cracking unit, is introduced into the process through line 1 at a rate of about 5,938 bbls/day (958.16 moles/hr). The olefinic feedstock is admixed in line 1 with about 54,034 bbls/day (7,699.74 moles/hr) of an isobutane-rich stream comprising recycled isobutane from line 2 and make-up isobutane entering the process through line 3 to provide about 7471.23 moles of isobutane per hour to the alkylation reactor 4. As hereinafter described, the recycled isobutane will further contain about 116.09 moles of hydrofluoric acid per hour. In any case, the resulting mixture is continued through line 1 to the alkylation reactor 4. The alkylation reactor is designed to function as a heat exchanger having multiple feed injection points—a design which is well known and therefore not illustrated. Hydrofluoric acid is charged to the alkylation reactor in an amount of approximately 95,724 bbls/day (58,776.5 moles/hr). This amount is inclusive of about 58,360 moles/hr recycled from a first acid settler 5 through line 6, 116.09 moles/hr recycled from an isostripper column 7 by way of line 2 in admixture with about 6697.6 moles of isobutane per hour, and 300.21 moles/hr of regenerated acid recycled from a second acid settler 8 through lines 9 and 6 in admixture with about 322.08 moles of isobutane per hour as hereinafter described. In the alkylation reactor 4, the isobutane/olefinic hydrocarbon volume ratio is about 13:1, and the acid catalyst/hydrocarbon volumetric ratio is about 1.48:1. The alkylation reactor is maintained at a pressure of about 233 psig, and the acid catalyst and reactant streams are introduced thereto at a temperature of about 100° F. The material balance around the alkylation reactor 4, exclusive of the acid catalyst, is presented in the following Table I, the concentration of the various components being given in terms of moles per hour.

TABLE I

| Component | Charge | Effluent |
|---|---|---|
| Ethane | 1.0 | 1.0 |
| Propylene | 294.12 | — |
| Propane | 632.21 | 649.68 |
| Butylenes | 277.60 | — |
| Isobutane | 7471.23 | 7203.83 |
| n-Butane | 547.75 | 552.89 |
| Amylenes | 2.99 | — |
| Isopentane | 87.16 | 107.12 |
| n-Pentane | 0.64 | — |
| $C_6+$ | 41.00 | 586.77 |
| Polymer Products | — | 0.18 |

As heretofore stated, the acid-catalyzed alkylation of an olefin with an isoparaffin is a highly exothermic reaction which must be tempered by adequate cooling means. In the process illustrated, the heat of reaction is approximately $21.6 \times 10^6$ BTU/hour, and said heat is removed through the use of about 8,685 gallons of 85° F. water per minute entering the reactor via line 10 and exiting by way of line 11 at a temperature of about 90° F. The total reaction mixture is withdrawn from the alkylation reactor 4 through line 12 at a temperature of about 100° F. and at a pressure of about 218 psig.

The alkylation reactor effluent is continued through line 12 into a first acid settler 5 wherein an acid phase is allowed to settle out as a hydrocarbon immiscible lower layer. The hydrofluoric acid catalyst is recovered from the acid settler 5 via line 6 at a rate of about 95,346 bbls/day (58,544.3 moles/hr), and at a pressure of about 203 psig. A major portion of this amount, around 95,046 bbls/day (58,360 moles/hr) is continued through line 6 and recycled to the alkylation reactor 4. The balance, approximately 184.3 moles/hr inclusive of polymer products, is diverted from line 6 through line 13 and delivered to the suction inlet of an eductor 14 at a pressure of about 200 psig.

The polymer products-containing hydrofluoric acid is drawn into and becomes entrained in a hydrocarbon stream passing through the eductor 14 from line 15 at a rate of about 325.86 moles/hr, said hydrocarbon stream being one portion of the bottoms effluent from a depropanizer column 16 recovered therefrom at a pressure of about 315 psig as hereinafter related. Said hydrocarbon stream, which serves as a hydrofluoric acid pumping means, comprises about 92 mole % isobutane, 2 mole % propane and 6 mole % n-butane.

Referring back to the first acid settler 5, a hydrocarbon-rich stream, comprising about 8,776.21 moles of hydrocarbon and 232.18 moles of hydrofluoric acid per hour, is withdrawn through an overhead line 17 at a temperature of about 100° F. and at a pressure of about 203 psig. This material is passed through a heat exchange means 18 and introduced into line 15' at a temperature approximating 170° F. The resultant acid-hydrocarbon stream is then continued through line 15' and discharged into the upper section of the isostripper column 7 at a pressure of about 150 psig. Field butane, at a temperature of about 100° F., enters the isostripper column 7 through line 19 in an amount of about 144.16 moles/hr. A normal butane-rich side cut is taken from the isostripper column via line 20 at a rate of around 96.59 moles/hr and caustic-treated for the removal of trace quantities of acid. The isostripper column is typically operated at a bottom temperature of about 371° F., and at a top temperature of about 140° F. The bottom pressure is generally maintained at about 160 psig, and the top pressure at about 152 psig. Hydrofluoric acid is recovered overhead from the isostripper column 7 at a rate of about 300.21 moles/hr in admixture with about 1091.41 moles/hr of $C_3$–$C_4$ hydrocarbons, and substantially free of the polymer products. The normally liquid alkylate product is recovered through line 22 at a rate of about 6,426 bbls/day (628.30 moles/hr), and said product is also caustic-treated for the removal of residual hydrofluoric acid. An isobutane-rich stream, in an amount of about 7620.4 moles/hr is recycled by way of line 2 to the alkylation reactor 4. Hydrofluoric acid in an amount of about 116.09 moles/hr is also recycled through line 2 as heretofore mentioned. In any case, the recycle stream in line 2 is increased in pressure to about 310 psig by means of pump 21. The component composition of the various charge and effluent streams around the isostripper column 7 is presented in the following Tables II and III:

TABLE II

| | Isostripper Feed Streams | |
|---|---|---|
| | Line 15' | Line 19 |
| Ethane | 1.0 | — |
| Propylene | — | — |
| Propane | 649.68 | 3.36 |
| Butylenes | — | — |
| Isobutane | 7504.44 | 67.85 |
| n-Butane | 559.18 | 70.41 |
| Amylenes | — | — |
| Isopentane | 108.12 | 1.64 |
| n-Pentane | — | 0.90 |
| $C_6+$ | 586.77 | — |
| HF Acid | 416.48 | — |
| Polymers | 0.18 | — |

TABLE III

| | Isostripper Effluent Streams | | | |
|---|---|---|---|---|
| | Line 23 | Line 2 | Line 20 | Line 22 |
| Ethane | 1.0 | — | — | — |
| Propylene | — | — | — | — |
| Propane | 183.6 | 469.60 | — | — |
| Butylenes | — | — | — | — |
| Isobutane | 868.76 | 6697.60 | 4.66 | 1.27 |
| n-Butane | 15.35 | 453.21 | 99.55 | 54.42 |
| Amylenes | — | — | — | — |
| Isopentane | 2.69 | 78.64 | 1.64 | 26.79 |
| n-Pentane | — | — | — | 0.90 |
| $C_6+$ | — | 41.0 | 0.07 | 545.70 |
| HF Acid | 300.39 | 116.09 | — | — |
| Polymers | — | — | — | 0.18 |

The overhead is continued through line 23 in admixture with hydrofluoric acid recycled through line 24 from an acid stripping column 25 at a rate of about 15.22 moles/hr, and the mixture is introduced into the aforementioned second acid settler 8.

Settled acid, in an amount of about 300.21 moles/hr, is recycled to the alkylation reactor 4 by way of lines 9 and 6, said acid being substantially free of the polymer by-products. Hydrocarbons, amounting to about 761.70 moles/hr, including about 15.22 moles/hr of hydrofluoric acid/hr, are introduced via line 26 into the upper ection of the depropanizer column 16. The top of the column is maintained at a temperature of about 140° F. and at a pressure of about 305 psig. A propane concentrate is recovered as an overhead stream in line 27 together with about 15.22 moles of acid/hr, and said stream is discharged into the acid stripping column 25. The depropanizer bottom temperature is about 220° F. and the bottom pressure is about 315 psig. The depropanizer column bottoms effluent, compressing about 589.37 moles of hydrocarbons/hr, is withdrawn through line 15 and utilized as follows: 263.51 moles are diverted through line 28 per hour for recycle to the alkylation reactor 4 via line 2, and 325.86 moles/hr are continued through line 15, an open block valve 29, the aforementioned eductor 14 and line 15' to serve as a pumping means for the hydrofluoric acid charged to the suction inlet of said eductor from line 13 as heretofore described. The material balance for the depropanizer column is set out in Table IV below:

TABLE IV

| Depropanizer Material Balance | | | |
|---|---|---|---|
| | Line 25 | Line 26 | Line 15 |
| Ethane | 1.0 | 1.0 | — |
| Propane | 188.16 | 176.99 | 11.17 |
| Isobutane | 546.68 | 2.97 | 543.71 |
| n-Butane | 34.49 | — | 34.49 |
| Isopentane | 2.69 | — | 2.69 |

Hydrofluoric acid, in an amount of about 15.22 moles/hr, is withdrawn as an overhead stream from the hydrofluoric acid stripping column 25 and recycled through line 24 and line 23 to the acid settler 8. About 176.66 moles of hydrocarbon are recovered from the hydrofluoric acid stripping column per hour through line 30. The hydrofluoric acid stripping column 25 functions at a top temperature of about 140° F., and at a pressure of about 310 psig. The bottom temperature is maintained at about 150° F., and the pressure at about 320 psig. Line 31 and block valve 32 are provided in the event that it becomes desirable to utilize the hydrofluoric acid stripper bottoms as the motive force to the eductor 14. In the same vein, a suitable portion of the isostripper column bottoms passing through line 2 can be diverted through line 33 and block valve 34 and line 15 to provide an alternate motive force to the eductor 14.

I claim as my invention:

1. A process for the hydrofluoric acid-catalyzed alkylation of an olefin with an isoparaffin utilizing an isoparaffin stripping column-integrated acid catalyst regeneration system which comprises the steps of:
    (a) reacting said olefin with said isoparaffin in an alkylation reaction zone in admixture with a hydrofluoric acid catalyst at alkylation reaction conditions resulting in a reaction product effluent comprising a normally liquid alkylate product, unreacted isoparaffin, hydrofluoric acid catalyst, and polymer products;
    (b) introducing said reaction zone effluent into a separation zone, and settling said mixture into an acid-immiscible hydrocarbon phase and a polymer-containing acid phase;
    (c) recovering and recycling a first portion of said acid phase to said reaction zone;
    (d) recovering and heating said hydrocarbon phase to increase the solubility potential of hydrofluoric acid therein;
    (e) recovering and transferring a second portion of said acid phase to the suction inlet of an eductor and entraining said acid phase in a $C_3$–$C_4$ paraffinic hydrocarbon pumping fluid charged therethrough;
    (f) admixing the acid-containing eductor effluent with said heated hydrocarbon phase; and,
    (g) introducing the resulting mixture into a stripping column and stripping a polymer-free acid catalyst therefrom by means of a counterflowing isoparaffin-containing stream, separating an intermediate isoparaffin fraction from said column, and recovering a polymer-containing, normally liquid, alkylate bottoms product.

2. The process of claim 1 further characterized in that said isoparaffin contains from about four to about seven carbon atoms per molecule.

3. The process of claim 1 further characterized in that said olefin contains from about three to about seven carbon atoms per molecule.

4. The process of claim 1 further characterized in that said isoparaffin is isobutane.

5. The process of claim 1 further characterized in that said olefin is propylene.

6. The process of claim 1 further characterized in that said olefin is a butylene.

7. The process of claim 1 further characterized in that said olefin is a mixture of propylene and butylenes.

8. The process of claim 1 further characterized in that said alkylating conditions include an isoparaffin/olefin molar ratio in the range of about 1.1:1 to about 20:1 and a temperature from about 0° F. to about 200° F.

9. The process of claim 1 further characterized with respect to step (e) in that said hydrocarbon pumping fluid is an isobutane-rich stream recovered as a bottoms fraction from a depropanizer column.

10. The process of claim 1 further characterized with respect to step (e) in that said hydrocarbon pumping fluid is a propane-rich stream recovered as a bottoms fraction from a hydrofluoric acid stripping column.

11. The process of claim 1 further characterized with respect to step (e) in that said hydrocarbon pumping fluid is an isobutane-rich stream recovered as a side cut from an isostripper column.

* * * * *